(12) United States Patent
Walish et al.

(10) Patent No.: US 10,933,227 B2
(45) Date of Patent: Mar. 2, 2021

(54) URETERAL STENT (71) Applicant: GYRUS ACMI, INC., Southborough, MA (US)

(72) Inventors: Judy L. Walish, West Roxbury, MA (US); Hui Tang, Action, MA (US); Thomas J. Holman, Princeton, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 0 days.

(21) Appl. No.: 15/829,092

(22) Filed: Dec. 1, 2017

(65) Prior Publication Data
US 2019/0167958 A1 Jun. 6, 2019

(51) Int. Cl.
A61M 27/00 (2006.01)
A61F 2/88 (2006.01)
A61L 31/04 (2006.01)
A61F 2/04 (2013.01)

(52) U.S. Cl.
CPC ......... *A61M 27/008* (2013.01); *A61F 2/885* (2013.01); *A61L 31/042* (2013.01); *A61F 2002/048* (2013.01)

(58) Field of Classification Search
CPC .... A61F 2/885; A61F 2002/047; A61F 2/042; A61M 27/008
See application file for complete search history.

(56) References Cited

U.S. PATENT DOCUMENTS

| | | |
|---|---|---|
| 4,531,933 A | 7/1985 | Norton et al. |
| 4,950,228 A | 8/1990 | Knapp, Jr. et al. |
| 4,990,133 A | 2/1991 | Solazzo |
| 5,518,498 A * | 5/1996 | Lindenberg ............... A61F 2/94 128/DIG. 25 |
| 5,520,697 A | 5/1996 | Lindenberg et al. |
| 5,647,843 A | 7/1997 | Mesrobian et al. |
| 5,681,274 A | 10/1997 | Perkins et al. |
| 5,795,319 A | 8/1998 | Ali |
| 6,332,892 B1 | 12/2001 | Desmond, III et al. |
| 6,709,465 B2 | 3/2004 | Mitchell et al. |
| 6,849,069 B1 | 2/2005 | Clayman et al. |

(Continued)

FOREIGN PATENT DOCUMENTS

| | | |
|---|---|---|
| CN | 201643330 U | 11/2010 |
| CN | 202154928 U | 3/2012 |

(Continued)

OTHER PUBLICATIONS

Extended European Search Report for European Application No. 18209356.7; dated Apr. 30, 2019.

(Continued)

*Primary Examiner* — Brian A Dukert
*Assistant Examiner* — Rebecca Lynee Zimmerman
(74) *Attorney, Agent, or Firm* — Schwegman Lundberg & Woessner, P.A.

(57) ABSTRACT

A ureteral stent that includes a tubular member and a retaining end adapted to be placed inside a kidney or a bladder of a patient. The retaining end includes a plurality of loops. Each of the loops are centered about a loop axis, and two or more of the loop axes extend in different directions relative to other loop axes.

20 Claims, 6 Drawing Sheets

(56) References Cited

U.S. PATENT DOCUMENTS

| | | | |
|---|---|---|---|
| 6,908,447 B2* | 6/2005 | McWeeney | A61F 2/0022 604/9 |
| 6,949,125 B2 | 9/2005 | Robertson | |
| 7,044,981 B2 | 5/2006 | Liu et al. | |
| 7,722,677 B2 | 5/2010 | Ward | |
| 8,007,540 B2 | 8/2011 | Robertson | |
| 8,252,065 B2 | 8/2012 | Ward | |
| 8,512,272 B2 | 8/2013 | Ostrovsky et al. | |
| 8,702,788 B2 | 4/2014 | Kheradvar et al. | |
| 8,840,660 B2 | 9/2014 | Weber | |
| 8,920,513 B2 | 12/2014 | Rickner | |
| 2001/0021835 A1* | 9/2001 | Mitchell | A61F 2/07 604/385.17 |
| 2004/0143209 A1 | 7/2004 | Liu et al. | |
| 2005/0240280 A1* | 10/2005 | Aliski | A61F 2/04 623/23.68 |
| 2006/0259151 A1 | 11/2006 | Ward | |
| 2007/0276466 A1 | 11/2007 | Lavelle et al. | |
| 2008/0249636 A1 | 10/2008 | Deal | |
| 2010/0100170 A1 | 4/2010 | Tan et al. | |
| 2010/0198359 A1 | 8/2010 | Ward | |
| 2011/0230950 A1 | 9/2011 | Knapp | |
| 2011/0320008 A1 | 12/2011 | Teague et al. | 623/23.65 |
| 2016/0157991 A1 | 6/2016 | Tan-Malecki et al. | |
| 2017/0119559 A1 | 5/2017 | Seguy et al. | |
| 2017/0333672 A1 | 11/2017 | Erbey, II et al. | |

FOREIGN PATENT DOCUMENTS

| | | |
|---|---|---|
| EP | 2749309 A1 | 7/2014 |
| EP | 3492135 A1 | 6/2019 |
| JP | 2019098182 A | 6/2019 |
| WO | WO-03079934 A1 | 10/2003 |
| WO | 2004/032795 A2 | 4/2004 |
| WO | 2004/032795 A3 | 4/2004 |
| WO | WO-2005102217 A1 | 11/2005 |
| WO | 2011/126572 A2 | 10/2011 |

OTHER PUBLICATIONS

"Chinese Application Serial No. 201811422658.6, Office Action dated Jun. 2, 2020", w/ English Translation, 23 pgs.

"European Application Serial No. 18209356.7, Response filed Dec. 3, 2019 to Extended European Search Report dated Apr. 30, 2019", 7 pgs.

"Japanese Application Serial No. 2018-223872, Examiners Decision of Final Refusal dated May 19, 2020", w/ English Translation, 5 pgs.

"Japanese Application Serial No. 2018-223872, Office Action dated Aug. 20, 2019", w/ English Translation, 11 pgs.

"Japanese Application Serial No. 2018-223872, Response filed Nov. 12, 2019 to Office Action dated Aug. 20, 2019", w/ English Translation, 13 pgs.

"Chinese Application Serial No. 201811422658.6, Response Filed Sep. 30, 2020 to Office Action dated Jun. 2, 2020", w/ English Claims and machine translation, 29 pgs.

"Japanese Application Serial No. 2018-223872, Response filed Sep. 17, 2020 to Examiners Decision of Final Refusal dated May 19, 2020", w/ English claims and machine translation, 26 pgs.

* cited by examiner

Fig - 14

URETERAL STENT

FIELD

These teachings relate to a medical device, and more particularly to a ureteral stent.

BACKGROUND

A ureteral stent may be placed inside a patient to assist in urinary drainage from a kidney to a bladder. For example, after some ureteral stone procedures, pieces or fragments of the stone or tumor can drop down into the ureter, which may disrupt or block the flow of urine from the kidney to the bladder. The ureteral stent may function to allow the ureter to dilate and provide for the stone or stone fragments to pass and allow urine to flow from the kidney to the bladder.

A ureteral stent generally comprises a tubular member that terminates at two opposing ends. One of the ends may be referred to as an upper or kidney end, which, as the name suggests, is placed in the kidney, and the other end may be a lower or bladder end, which is placed in the bladder. The tubular member is positioned in the urinary tract between the kidney and the bladder. One or both of the ends may include a retention feature that is adapted to retain the stent in the patient and restrict or prevent the upward and/or downward migration of the stent. However, one or both of the retention features may produce adverse effects or patient discomfort including: hemorrhage, a continual urge to urinate, and trigone irritation.

It may therefore be desirable to improve the current state of the art by providing a ureteral stent that can be placed inside a patient to provide a passageway for urinary drainage from a kidney to a bladder, while also reducing or eliminating patient discomfort.

Some examples of ureteral stents are disclosed in U.S. Pat. Nos. 4,531,933, 4,950,228, 5,520,697, 5,647,843, 5,681,274, 5,795,319, 6,949,125, 8,007,540, 8,920,513; and in US Patent Application Publication Nos. 2004/0143209 and 2016/0157991, all of which are hereby incorporated by reference for all purposes.

SUMMARY

These teachings provide a ureteral stent that includes a tubular member and a retaining end adapted to be placed inside a kidney or a bladder of a patient. The retaining end includes a plurality of loops. Each of the loops are centered about a loop axis, and two or more of the loop axes extend in different directions relative to other loop axes.

These teachings also provide a ureteral stent comprising a tubular member and a retaining end adapted to be placed inside a kidney or a bladder of a patient. The retaining end comprises one or more sections having one or more openings.

DETAILED DESCRIPTION

These teachings are directed to a stent. The stent may be a medical stent. The stent may be any stent, such as a ureteral stent. The ureteral stent may function to assist in fluid or urinary drainage from the kidney to the bladder in patients. For example, after some ureteral stone or tumor medical procedures, pieces or fragments of the stone or tumor can drop down into the ureter, which may disrupt or block the flow of urine from the kidney to the bladder. The ureteral stent may function to allow the ureter to dilate, which may provide for the stone or stone fragments to pass and allow fluid or urine to flow from the kidney to the bladder.

The stent may comprise a tubular member. The tubular member may be placed in the urinary tract of a patient. The tubular member may extend between two opposing ends, one or both of which may be retaining ends. The tubular member may be a generally hollow member that includes a through bore, opening, or lumen that extends from one retaining end to another end.

The through bore, opening, or lumen may function to allow a wire to pass through the tubular member to assist with inserting and removing the stent in the patient. The through bore, opening, or lumen may have a suitable size or diameter to be able to insert and remove the wire. The diameter may be on the order of about 0.040 inches to about 0.045"; however, larger and smaller sizes may be used depending on the specific use for the stent. Once inserted into the patient, the through bore or opening defined in the tubular member may also function to allow urine or other fluids to pass from the kidney to the bladder. The through bore may extend along a longitudinal axis of the tubular member.

The tubular member may have any suitable cross section. For example, the cross section of the tubular member may be generally round or spherical, flattened, elliptical, or oval shaped. The cross-section may be generally consistent between the two opposing ends (i.e., generally round along an entire length of the tubular member); or the cross section of tubular member may be generally inconsistent along an entire length thereof (i.e., some portions of the tubular member may have a generally round cross section and then other parts may have an oval or flat cross section).

The cross section of the tubular member may have any suitable thickness. The thickness of the tubular member may be generally constant between the opposing ends, or the thickness of the tubular member may vary or change along its length between larger and smaller cross sections, or different shapes.

The size or diameter of the tubular member, the retaining ends, could be on the order from about 0.1 mm to about 1.5 mm. In some configurations, it may be preferable for the diameter of the tubular member and/or retaining ends to be less than to 2.3 mm. The size of the tubular member and/or retaining ends may have a French size (F) on the order from about 1 F to about 16 F; however, larger or smaller French sizes may be considered depending on the specific application of the stent.

The length of the stent (i.e., the tubular member with or without the retaining ends) may be on the order of about 50 mm to about 350 mm; however, longer or shorter lengths may be considered depending on the specific application of the stent.

The stent may comprise one or more retaining ends. The one or more retaining ends may function to restrict or prevent the stent from moving inside a patient after the stent is implanted inside the patient. The one or more retaining ends may be anti-migration features. The one or more retaining ends are adapted to contact or provide resistance against the openings of the body passageway and thus helps prevent the stent from moving or migrating through the body passageway. The one or more retaining ends disclosed herein are adapted to minimize tissue irritation because of their flexible configuration. The one or more retaining ends disclosed herein are adapted to minimize tissue irritation by way of reducing the number of contact areas and force between the retaining end and tissue, kidney, or bladder. For example, only a tangent portion or area of one or more of the bows or loops my contact the tissue, kidney, or bladder, which may lead to less tissue irritation by the stent compared to if an entire retaining end of the stent was to contact the tissue, kidney, or stent. For example, the areas of the retaining end between the openings in the bulges may contact the tissue, kidney, or bladder, which may lead to less tissue irritation by the stent compared to if an entire retaining area was to contact the tissue, kidney, or bladder.

One of the ends may be adapted to be placed in a kidney of a patient, and the other opposing end may be adapted to be placed a bladder of the patient.

The one or more ends, the tubular member, or a combination thereof may change between an undeployed configuration and a deployed configuration.

Figures 1, 2:
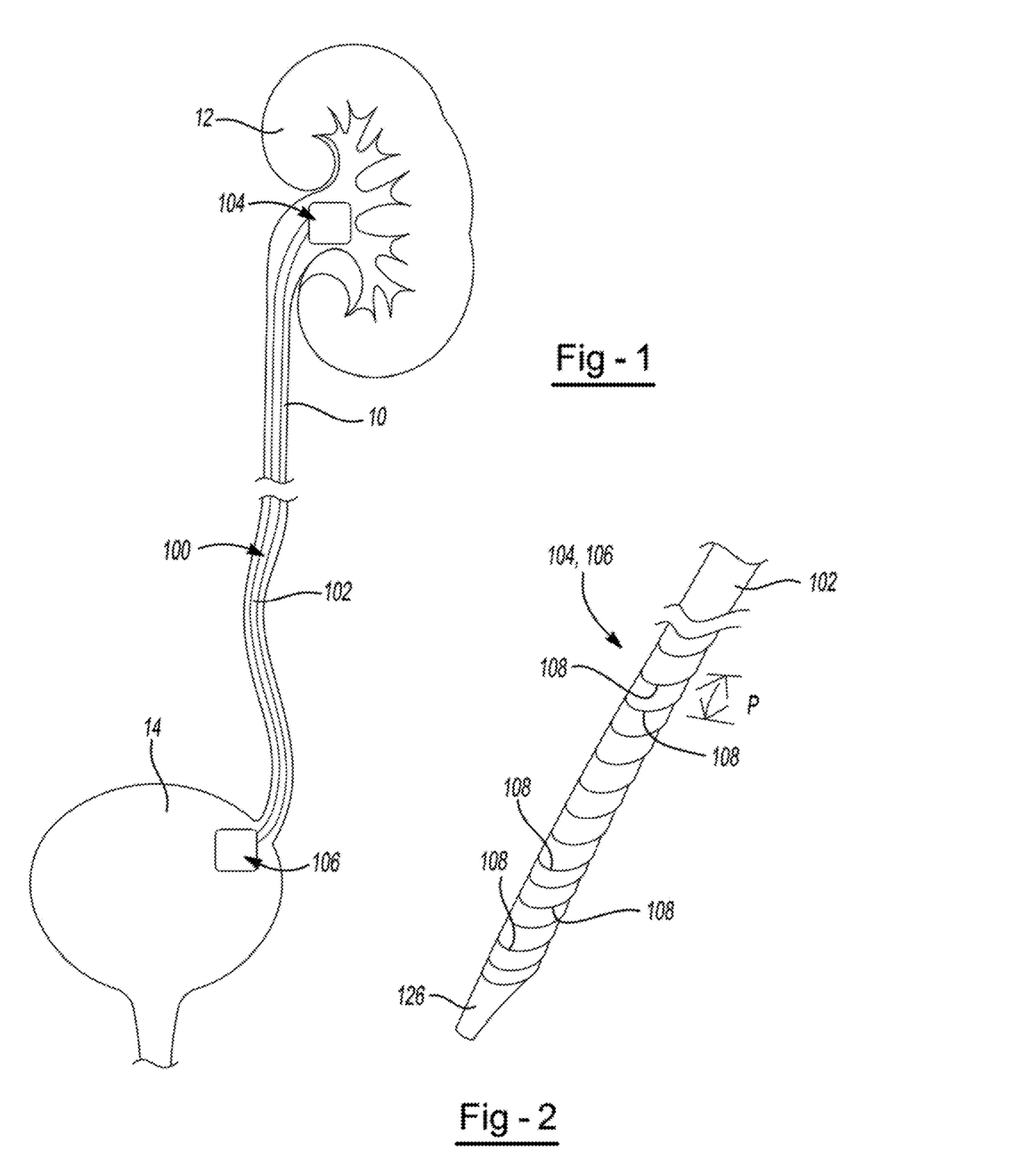
FIG. 1 illustrates a ureteral stent located in a kidney, ureter, and bladder of a patient.
FIG. 2 is a front view of a retaining end of the ureteral stent in a non-deployed configuration.
Figure 6:
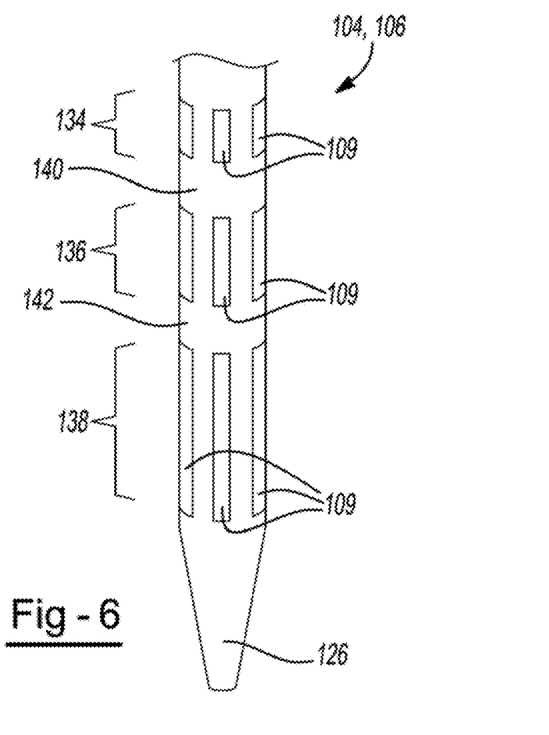
FIG. 6 is a front view of a retaining end of the ureteral stent in a non-deployed configuration.

In the undeployed configuration, the retaining end may be generally straight or linear such as the ends illustrated in FIGS. 2 and 6. In the undeployed configuration, the retaining end may be generally free from comprising any loops, or bows, or bulges. In the undeployed configuration, the retaining end may be free from meandering along a path where the retaining end crosses under or over itself.

The undeployed configuration may be maintained before the stent is inserted into the patient, for example, during shipping from the stent supplier to the hospital or clinic. The undeployed configuration may be maintained while the stent is being inserted or implanted into the patient. The undeployed configuration may be maintained while the stent is being removed from the patient. The undeployed configuration may be maintained when or while the guidewire is inserted into the tubular member and/or retaining ends. The undeployed configuration may be maintained when there is little or no pressure acting on the stent or retaining end from an inside of the tubular member or stent at the through bore. The pressure may be from urine or other fluids passing through the tubular member or retaining ends. The pressure may be fluid urine or other fluids containing an outside surface of the tubular member or retaining end. The undeployed configuration of the stent or retaining end may be maintained when the stent is in a room temperature or a cool temperature, and the deployed configuration may be achieved when the stent or retaining end is heated or in a warm environment, such as inside the patient.

In the deployed configuration, the retaining end may extend or meander or be maintained in a generally non-linear or curved configuration. In the deployed configuration, the retaining end may meander and cross over or under itself at one or more places, two or more places, three or more places, 6 or more places 9 or more places 15 or more places, etc. In the deployed configuration, the retaining end may be intertwined in itself in one or more loops, bows, knots, petals, curls, coils, twists, or a combination thereof. In the deployed configuration, the retaining end may comprise two or more loops, three or more loops, four or more loops, six or more loops, 9 or more loops, etc. In the deployed configuration, the retaining end may be twisted around or about a longitudinal axis of the tubular member and/or retaining end. In the deployed configuration, the retaining end may comprise one or more bulges, 2 or more bulges, 3 or more bulges 4 or more bulges, 6 or more bulges 9 or more bulges, etc.

The deployed configuration may be maintained while the stent is located inside the patient. The deployed configuration may be achieved and maintained after the guidewire is removed or withdrawn from inside the tubular member and/or retaining ends. The deployed configuration may be maintained when there is pressure acting on the through bore of the stent or retaining end from an inside of the tubular member or stent. The pressure may be from urine or other fluids passing through the tubular member or retaining ends, which may cause the retaining end to deploy and form loops or bulges.

The stent has a sufficient coil strength to maintain one or both of the ends in the deployed configuration and resist peristaltic and body movement forces. For example, the coil strength may be on the order of about 2.0 grams to about 100 grams.

The tubular member may comprise one or more openings. The one or more openings may be cuts, apertures, holes, and/or pores. The one or more openings may be an absence of material in the tubular member, retaining end(s), or both. The one or more openings may be in fluid communication with the through bore or lumen that extends through the tubular member, retaining end(s), or both. The one or more openings may function to allow fluid to pass through a wall defining the tubular member, retaining end(s), or both from inside the sent to outside the stent, or from outside the stent to inside the stent. These openings may be of any size that allows fluids to pass through the wall. The openings may also function to add to flexibility of the tubular member, retaining end(s), or both, which may be desirable to maneuver the tubular member or stent though the patient during implantation of the stent. The openings may also function to add to flexibility of the tubular member, retaining end(s), or both, which may allow the tubular member, retaining end(s), or both to move and adapt to movement of the patient. The openings may extend generally perpendicularly or angled relative to a longitudinal axis of the tubular member, retaining end(s), or both or the lumen or through bore that extends along a longitudinal axis of the tubular member.

The one or more openings may have any size or shape. For example, the one or more openings may be circular, round, spherical, rectangular, square, or a combination thereof. The shape, size, placement, and orientation of the one or more openings may contribute to the shape, size, placement, and orientation of a bulge formed in the areas or sections having the openings when the retaining end is in the deployed configuration.

The stent may comprise one or more cuts. The one or more cuts may function to provide the tubular member, one or more of the ends, or a combination thereof with flexibility and determine the shape that the end(s) form in the deployed configuration. The cuts may be formed into an outer surface of the tubular member, one or more of the ends, or both. The cuts may protrude all the way through the outer surface of the tubular member and/or ends to the lumen or through bore disposed therein, or the cuts may only project partly through the outer surface of the tubular member and/or retaining end(s).

The cuts may extend along an entire length of the stent or tubular member, or retaining end, or only in the area where the retiming feature is to be formed. The cuts may be along a length of the retaining end about 4 cm to about 6 cm long. However, longer and shorter lengths are envisioned depending on the particular use and configuration of the sent.

The cuts may be a spiral cut. The cuts may be concentric, spaced apart cuts. The cuts may be formed by laser cutting. The pitch defined between adjacent cuts may be optimized to increase or decrease flexibility of the tubular member and/or the ends. For example, a smaller pitch may function to maintain the tubular shape of the tubular member and/or ends, but make the tubular member and/or ends more flexible. A larger pitch may function to provide for the tubular member and/or the ends to be formed into a desired shape, for example, for the ends to form into the shapes illustrated in the figures in the deployed configuration.

The one or more ends may have a terminal end. The terminal end may also be referred to as a kidney tail or bladder tail depending on where the terminal end is located. In order to reduce tissue irrigation, in the deployed configuration, the terminal end may be provided inwardly, or curved inwardly, or tucked inwardly away from tissue of the kidney and/or bladder. That is, the terminal end may be tucked or point inside a foot print of the entire terminal end in the deployed configuration. This configuration of the terminal end may advantageously prevent the terminal end from contacting tissue, especially when a patient moves and the stent moves or adjusts its position inside the patient.

The stent may be made of one or more materials. The one or more materials of the stent, the tubular member, the retaining ends, or a combination thereof may resist tissue adherence and encrustation. The one or more materials may be soft or flexible such that the stent and/or retaining ends may conform to a lumen or passageway of a patient into which the stent is inserted. The one or more materials may be strong enough such that the stent and/or retaining ends provide support for the body passageway or maintain the body passageway at a certain diameter.

The one or more materials of the stent, the tubular member, the retaining ends, or a combination thereof may comprise one or more of: silicone, polyurethane, polyethylene blend, polytetrafluoroethylene (PTFE), thermoplastic polyurethane (TPU), polyolefin elastomer (POE), Ethylene-vinyl acetate (EVA), Polystyrene-butadiene-styrene (SBS), silicone rubber, Nylon, Polyethylene or polythene (PE), polypropylene (PP), thermoplastics, C-Flex™, Percuflex™, Tecoflex™; Pebax®, stainless steel, metal, a metal alloy, Nitinol materials, nickel, titanium alloy super alloy, chromium cobalt, or a combination thereof. The material may comprise a shape memory material. The tubular member and/or retaining ends may comprises two or more materials (i.e., dual durometer or multi-durometer) that transition from a firm material at the tubular member to a soft or flexible material at the retaining ends. The material may be a swelling polymer that is adapted to expand when in contact with a fluid or when subjected to an increase in temperature, such as for example when the stent is located inside the patient.

The stent may be inserted or implanted inside a patient according to a method. The method may comprise one or more discrete steps. It is understood that one or more of the steps disclosed herein may be combined, separated into additional separate steps, omitted, repeated, or performed in one or more orders.

The method may include a step of inserting a guide wire into the patient and advancing the guidewire into the bladder and then into the kidney. The method then includes a step of loading or feeding the stent onto the guidewire. The method includes a step of pushing or feeding the stent along the guidewire into the patient. During the pushing or feeding step, the stent and/or the ends thereof are in an undeployed configuration and are maintained in the undeployed configuration by the guide wire inside the stent. After the ends of the stent are located in the kidney and bladder of the patient, the method includes a step of withdrawing the guidewire from the patient. During or after the withdrawing step, one or both of the ends may move into the deployed configuration to help reduce, minimize or to prevent migration of the stent inside the patient. The stent may then remain inside the patient to allow the ureter to dilate, which may provide for the stone or stone fragments to pass and allow urine to flow from the kidney to the bladder. The stent may remain permanently in the patient. The stent may be made of a biodegradable material where the stent dissolves or degrades inside the patient over time. The stent may be removed from the patient by inserting another guidewire into the patient and through the stent. After the guidewire is fed back into the stent and into the corresponding ends, the corresponding ends of the stent may revert back into the nondeployed configuration. With the ends in the non-deployed configuration, the stent and the guidewire may then be removed from the patient.

FIG. 1 illustrates a ureteral stent 100. The ureteral stent 100 comprises a tubular member 102. The tubular member 102 is illustrated inside a urinary tract 10 of a patient. The ureteral stent 100 comprises a first retaining end 104 and a second retaining end 106 extending from opposing sides of the tubular member 102. The first retaining end is illustrated inside a kidney 12 of the patient, and an opposing second retaining end 106 is illustrated inside a bladder 14 of the patient.

FIG. 2 illustrates a portion of the tubular member 102 and a retaining end that may be the first and/or the second retaining end 104, 106. The retaining end 104, 106 illustrated in FIG. 2 is in the non-deployed configuration.

The retaining end 104, 106 may comprise a plurality of cuts, slits, recesses, openings, or grooves 108 (hereafter "cuts") disposed around an outer surface thereof. The cuts 108 may be an at least partial absence of material that extends into a thickness of the retaining end 104, 106. The cuts 108 may be a single, continuous spiral that extends the entire length of the retaining end 104, 106, from the tubular member 102 to a terminal end 126 of the retaining end 104, 106. Alternatively, the cuts 108 may be individual rings that extend around an outer surface of the retaining end 104, 106. Alternatively, the cuts 108 may be a combination of one or more helical spirals and one or more individual rings. The pitch P, or the distance defined between each of the cuts 108 may be constant or consistent along a length of the region of the retaining end 104, 106 that includes the cuts 108, or the pitch P can vary or change. For example, the pitch P can be adjusted to optimize flexibility of the retaining end 104, 106 so that the stent 100 can be easily maneuvered inside the patient when the stent 100 is inserted into the patent or while being removed from the patient. The pitch P can be adjusted to optimize flexibility of the retaining end 104, 106 so that the stent 100 can move or adapt to normal movements of the patient. The pitch P can also vary to optimize the shape(s) formed by the retaining end 104, 106 when the retaining end 104, 106 is in a deployed configuration, such as those illustrated in the following FIGS. 3-5.

Figure 3:
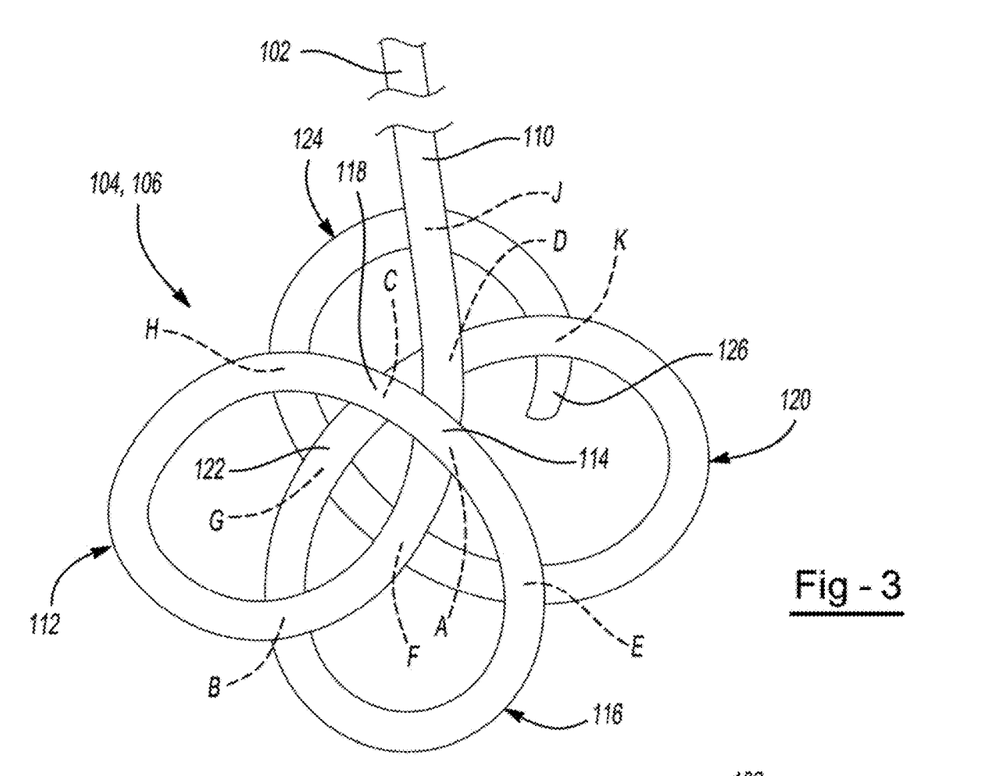
FIG. 3 is a front view of the retaining end of the ureteral stent of FIG. 2 in a deployed configuration.

FIG. 3 illustrates the retaining end that may be the first and/or the second retaining end 104, 106. The retaining end 104, 106 is illustrated in the deployed configuration.

The retaining end 104, 106 comprises a generally linear portion 110 that extends from an end of the tubular member 102. From the generally linear portion 110, the retaining end 104, 106 extends along a meandering or winding or non-linear path to form plurality of loops or bows.

For example, following the retaining end 104, 106 along a path from the generally linear portion 110 to the terminal end 126 of the retaining end 104, 106, the retaining end 104, 106 comprises a first loop 112 that begins and ends at approximately position 114 on the retaining end 104, 106. A second loop 116 begins at approximately position 114 and ends at approximately position 118 on the retaining end 104, 106. A third loop 120 begins at approximately position 118 and ends approximately position 122 on the retaining end 104, 106. A fourth loop 124 begins at approximately position 122 and ends approximately position 126 on the retaining end 104, 106, which may also be referred to as the terminal end of the retaining end 104, 106. The terminal end 126 is positioned or curved or tucked inwardly and protected within a footprint of all of the loops 112, 116, 120, 124 so that the terminal end 126 does not project outside of the loops and is not exposed directly to tissue, which may result in irritation of the end 126 was to come into contact with and poke the tissue.

Each of the loops 112, 116, 120, 124 are centered about their own loop axis. Each loop axis is different than any of the other loop axes. Each loop axis is offset, spaced apart from, and extends in a different location than any other loop axis. Stated another way, none of the loop axes are the same as, common, coaxial, and/or shared with other loop axes.

Loops 112 and 120, or the loop axis of each of loops 112 and 120, are laterally offset or offset on opposing sides from the linear portion 110 or tubular member 102 when the end 104, 106 is viewed from the front as shown in FIG. 3. Stated another way, loop 112 or its axis is offset to the left of the linear portion 110 or tubular member 102, and loop 120 or its axis is offset to the right of the linear portion 110 or tubular member 102.

Loops 116 and 124 have a loop axis that is generally aligned with the linear portion 110 or tubular member 102 when the end 104, 106 is viewed from the front as shown in FIG. 3.

A footprint, circumference, or perimeter of each of the loops 112, 116, 120, 124 is offset, spaced apart from, or in a different location all other loops 112, 116, 120, 124. Stated another way, no single loop 112, 116, 120, 124 is stacked or entirely located on top of or below another loop 112, 116, 120, 124. When viewing the end 104, 106 from the front view as shown in FIG. 3, at least a portion of every loop 112, 116, 120, 124 overlaps all other loops 112, 116, 120, 124.

Between the linear portion 110 and the terminal portion 126, the retaining end 104, 106 extends or meanders along an irregular, curved, non-linear path, and crosses over or under itself therebetween.

For example, following the end 104, 106 in a direction beginning at the generally linear portion 110 and ending at terminal end 126, the retaining end 104, 106 crosses over itself once at approximately position A, and then crosses under or behind itself at approximately positions B, C, D, E, F, G, H, J, K.

The size of the loops 112, 116, 120, 124, the general shape of the loops 112, 116, 120, 124, and where the retaining end 104, 106 crosses under or over itself may be dictated or controlled by the location, pitch P, and general shape of the cuts 108 (FIG. 2).

Figure 4:
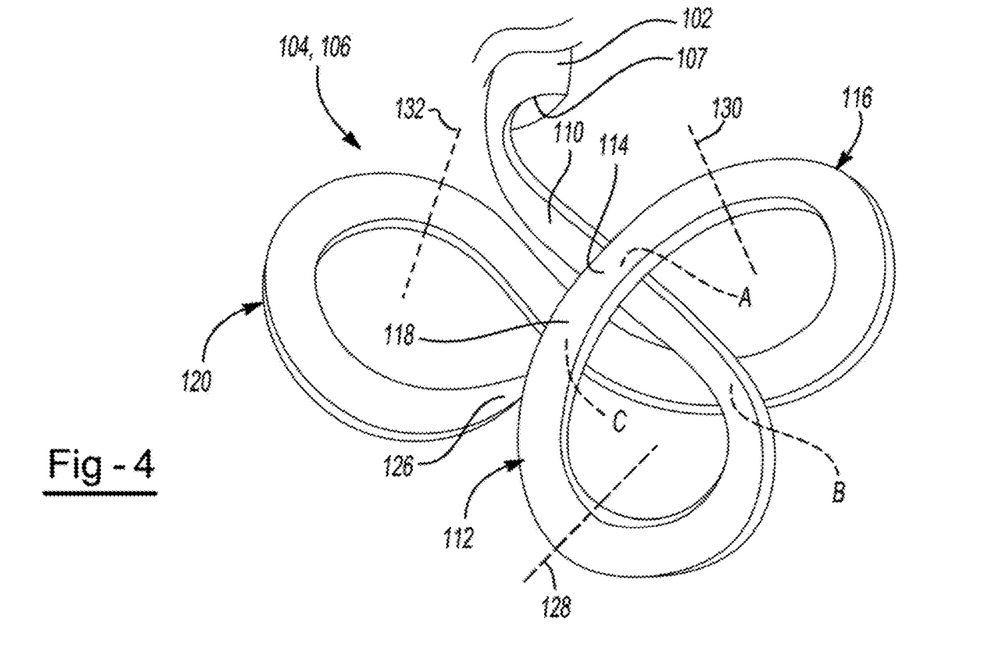
FIG. 4 is a perspective view of the retaining end of the ureteral stent of FIG. 2 in a deployed configuration.

FIG. 4 illustrates the retaining end that may be the first and/or the second retaining end 104, 106. The retaining end 104, 106 is illustrated in the deployed configuration.

The retaining end 104, 106 comprises a generally linear portion 110 that extends from an end of the tubular member 102 and terminates at terminal end 126. From the generally linear portion 110, the retaining end 104, 106 extends along a meandering or winding or non-linear path forming a plurality of loops.

For example, following the retaining end 104, 106 along a path from the generally linear portion 110 to the terminal end 126, the retaining end 104, 106 comprises a first loop 112 that begins and ends at approximately position 114 on the retaining end 104, 106. A second loop 116 begins at approximately position 114 and ends at approximately position 118 on the retaining end 104, 106. A third loop 120 begins at approximately position 118 and ends approximately position 126 on the retaining end 104, 106, which may be the terminal end of the retaining end 104, 106. The terminal end 126 is positioned or curved inwardly and protected within the loops 112, 116, 120, so that the terminal end 126 is not exposed directly to tissue, which may result in irritation of the end 126 was to come into contact with and poke the tissue.

Each of the loops 112, 116, 120, are centered about their own respective loop axis 128, 130, 132. Each loop axis 128, 130, 132 is different than any other loop axis 128, 130, 132. Each loop axis 128, 130, 132 is offset, spaced apart from, angled in a different direction, or located in a different location than any other loop axis. Stated another way, none of the loop axes 128, 130, 132 are the same as, common, coaxial, parallel to, or shared with other loop axes 128, 130, 132.

Loops 116 and 120, or the loop axis 130, 132 of each of the respective loops 112 and 120, are laterally offset from the linear portion 110 or tubular member 102 when the end 104,

106 is viewed from the view shown in FIG. 4. Loop 112 is generally aligned with the tubular member 102.

A footprint, circumference, or perimeter of each of the loops 112, 116, 120, is offset, spaced apart from, or in a different location than all other loops 112, 116, 120. This means that no single loop 112, 116, 120 is stacked or entirely located on top of or below another loop 112, 116, 120.

Each of the loops 112, 116, 120 are arranged or contained in a loop plane. Each loop plane is different than any other loop plane. This means that no loop plans are the same or coplanar. No loop plans are arranged parallel to one another. Moreover, each loop plane extends in a different direction than any other loop plane, or is angularly different than any other loop plane. Each of the loops 112, 116, 120 are twisted relative to each other.

Between the linear portion 110 and the terminal portion 126, the retaining end 104, 106 extends or meanders along an irregular, curved, non-linear, and crosses over or under itself.

For example, following the end 104, 106 along a path starting from the linear portion 110 to the terminal end 126, the retaining end 104, 106 crosses over itself once at approximately position A, and then crosses under or behind itself at approximately positions B, and C.

The size of the loops 112, 116, 120, the general shape of the loops 112, 116, 120, where the retaining end 104, 106 crosses under or behind or over itself may be dictated by position and shape of the cuts 108 and/or the pitch P of the cuts 108 (FIG. 2).

The tubular member 102 comprises a through bore 107 (See FIG. 4). The through bore 107 may extend between the two opposing ends 104, 106 of the stent 100. The through bore 107 may provide a passageway for urine or other fluids to pass between the kidney and bladder. The through bore 107 may provide a passageway for a guidewire to be passed through the tubular member 102 and/or the stent 100.

The tubular member 102 comprises a through bore 107. The through bore 107 may extend between the two opposing ends 104, 106 of the stent 100. The through bore 107 may provide a passageway for urine or other fluids to pass between the kidney and bladder. The through bore 107 may provide a passageway for a guidewire to be passed through the tubular member 102 and/or the stent 100.

Figure 5:
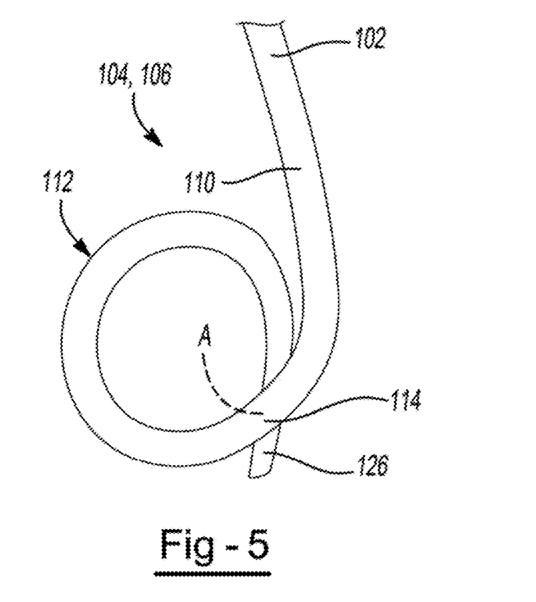
FIG. 5 is a front view of the retaining end of the ureteral stent of FIG. 2 in a deployed configuration.

FIG. 5 illustrates the retaining end that may be the first and/or the second retaining end 104, 106. The retaining end 104, 106 is illustrated in the deployed configuration.

The retaining end 104, 106 comprises a generally linear portion 110 that extends from an end of the tubular member 102. From the generally linear portion 110, the retaining end 104, 106 extends along a meandering, non-linear path forming a loop 112. The loop 112 begins and ends at approximately position 114. The retaining end 104, 106 crosses behind itself at approximately position A. The retaining end 104, 106 terminates at position 126. The size of the loop 112, the general shape of the loop 112, where the retaining end 104, 106 crosses under or over itself may be dictated by position and shape of the cuts 108 and/or the pitch P of the cuts 108 (FIG. 2).

FIG. 6 illustrates a retaining end that may be the first and/or the second retaining end 104, 106. The retaining end 104, 106 illustrated in FIG. 6 is in the non-deployed configuration.

The retaining end 104, 106 comprises a plurality of openings 109. The openings 109 may be an absence of material that extends into a thickness of the retaining end 104, 106. The openings 109 may be in communication with the through bore 107 defined in the tubular member 102 (FIG. 4, for example), and fluid or urine to pass from the through bore 107 through the openings 109.

The openings 109 may be arranged in one or more sections 134, 136, 138 on the retaining end 104, 106. Portion 140 is defined between the sections 134, 136 and may be substantially free of any openings 109. Portion 142 is defined between the sections 136, 138 and may be substantially free of any openings 109.

The openings 109 in each of the sections 134, 136, 138 may be disposed around an entire outer surface of the retaining end 104, 106, or only around a selected portion thereof. All of the openings 109 in each section 134, 136, 138 may be the same size, or the openings 109 in each section 134, 136, 138 may have different sizes.

The openings 109 may increase in size or length longitudinally in the sections 134, 136, 138 closest to the terminal end 126 of the retaining end 104, 106. For example, openings 109 in section 138 may be larger or longer in length than the openings 109 in section 136, and the openings 109 in section 136 may be larger or longer in length than the openings 109 in section 134.

Figure 7:
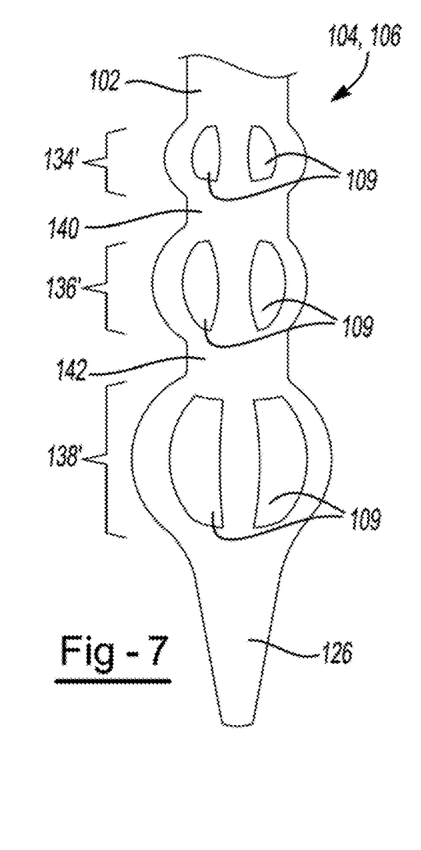
FIG. 7 is a front view of the retaining end of the ureteral stent of FIG. 6 in a deployed configuration.

FIG. 7 illustrates the retaining end 104, 106 of FIG. 6 in the deployed configuration.

In the deployed configuration, outwardly or radially extending bulges 134', 136', and 138' are formed at each of the sections 134, 136, 138 (FIG. 6). One or more of the bulges 134', 136', and 138' may be generally spherically-shaped. The bulges 134', 136', and 138' may be larger in size closest to the terminal end 126 of the retaining end 104, 106. For example, the bulge 138' may be larger or have a larger diameter than the bulge 136', and the bulge 136' may be larger or have a larger diameter than the bulge 134'. The relative sizes of the bulges 134', 136', and 138' may correspond to a length of size of the openings 109 in each section 134, 136, 138 (FIG. 6). That is, the larger or longer the opening 109 in each section, the larger the bulge. The bulges 134', 136', and 138' may be formed by a pressure being exerted on an interior surface or exterior surface of the tubular member 102 or retaining end 104, 106. The pressure may be fluid pressure, which may be urine or other bodily fluids being pass through the stent 100, for example, when fluid is communicated from a kidney to bladder and passes through the stent 100.

The portions 140, 142 defined between the respective bulges 134' and 136', and 136' and 138' are smaller in size or diameter than the bulges or sections 134', 136', and 138'. The size or diameter of one or both of the portions 140, 142 may be generally the same as the remainder of the tubular member 102.

Figure 8:
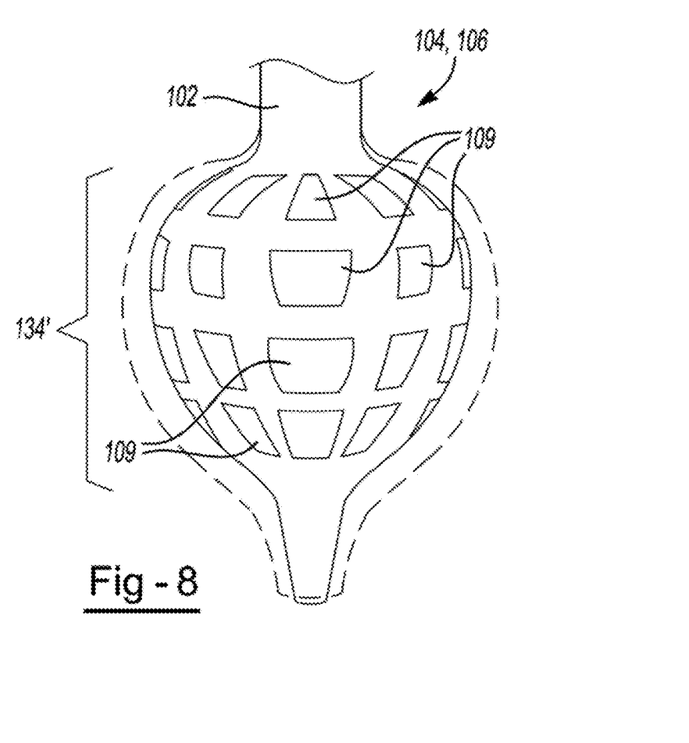
FIG. 8 is a front view of a retaining end of a ureteral stent in a deployed configuration.

FIG. 8 illustrates the retaining end 104, 106 in the deployed configuration. The non-deployed configuration of FIG. 8 may look substantially similar to the non-deployed configuration illustrated in FIG. 6, except that the retaining end 104, 106 only comprises one section, for example, only section 134. Accordingly, the retaining end 104, 106 of FIG. 8 only comprises one radially extending bulge 134'. The bulge 134' may be formed by a pressure being exerted on an interior surface of the tubular member 102 or retaining end 104, 106. The pressure may be fluid pressure, which may be urine or other bodily fluids being pass through the stent 100, for example, when fluid is communicated from a kidney to bladder and passes through the stent 100.

FIGS. 9-14 illustrate graphs of Stress ($\sigma$) applied on the stent vs. % of Surface area of stent ($S_0$)/Surface area of stent having cuts (S) (i.e., $S_0/S$). Flugge's formulation (EQ. 1 below) for the linear theory of orthotropic cylindrical shell was adopted to calculate instability of the stent 100 under external pressure. The external pressure may be fluid passing through or around the stent 100, movement of the patent, etc. Weibull Modulus formulation (EQ. 2 below) has been proposal for stress on the stent 100.

$$P_{cr}=[2\pi E t^2(t/R)^{1/2}/[3(6)^{1/2}(1-\mu^2)^{3/4}RL]]*10197.2 \qquad \text{EQ. 1:}$$

In EQ. 1 above, R=radius of the stent 100 (mm); L=length of stent 100 (mm); t=thickness of stent 100 (mm); Pcr=critical pressure (cmH2O, 1 MPa=10197.2 cmH2O); E=modulus of elasticity (MPa); and μ=Poisson's ratio (μ=0.5 was selected).

$$\sigma/\sigma_0=(S_0/S)^{(1/m)} \qquad \text{EQ. 2:}$$

In EQ. 2 above, σ=Stress of stent 100 with cuts 108; $\sigma_0$=Characteristic stress of stent 100 under critical pressure condition; $S_0$=Surface area of stent 100; S=Surface area of stent 100 with cuts 108; m=Weibull modulus (m=−1 was selected); $S_0$/S*100=effective surface (%).

A pressure in the renal artery during initial perfusion or passage of fluid through in the kidneys is on the order of about 40-60 cm H2O. However, for safety factor, a pressure range of 200 cm H2O to 225 cm H2O was used, which is denoted as the dashed oval in the graphs in FIGS. 9-14.

Figure 9:
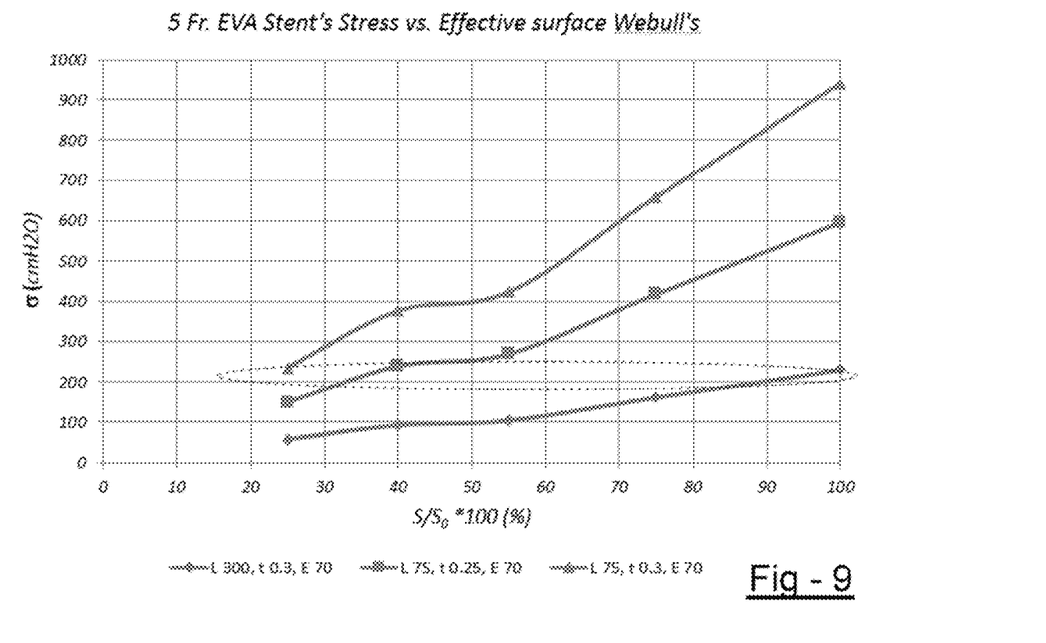
FIG. 9 is a graph illustrating Stress ($\sigma$) on the stent vs. % of Surface area of stent ($S_0$)/Surface area of stent having cuts (S) (i.e., $S_0/S$); the stent having a 5 Fr. size and made of EVA material.

Referring specifically to FIG. 9, three different stents having a 5 Fr. size made of EVA material having a modulus of elasticity of 70 MPA were tested.

As illustrated in FIG. 9, a first stent with a length of 300 mm and thickness of 0.3 mm fell within the pressure range of 200 cm H2O to 225 cm H2O at about 82 S/$S_0$ to about 100 S/$S_0$. A second stent with a length of 75 mm and thickness of 0.25 mm fell within the pressure range of 200 cm H2O to 225 cm H2O at about 32 S/$S_0$ to about 51 S/$S_0$. A third stent with a length of 75 mm and thickness of 0.30 mm fell within the pressure range of 200 cm H2O to 225 cm H2O at about 25 S/$S_0$.

Figure 10:
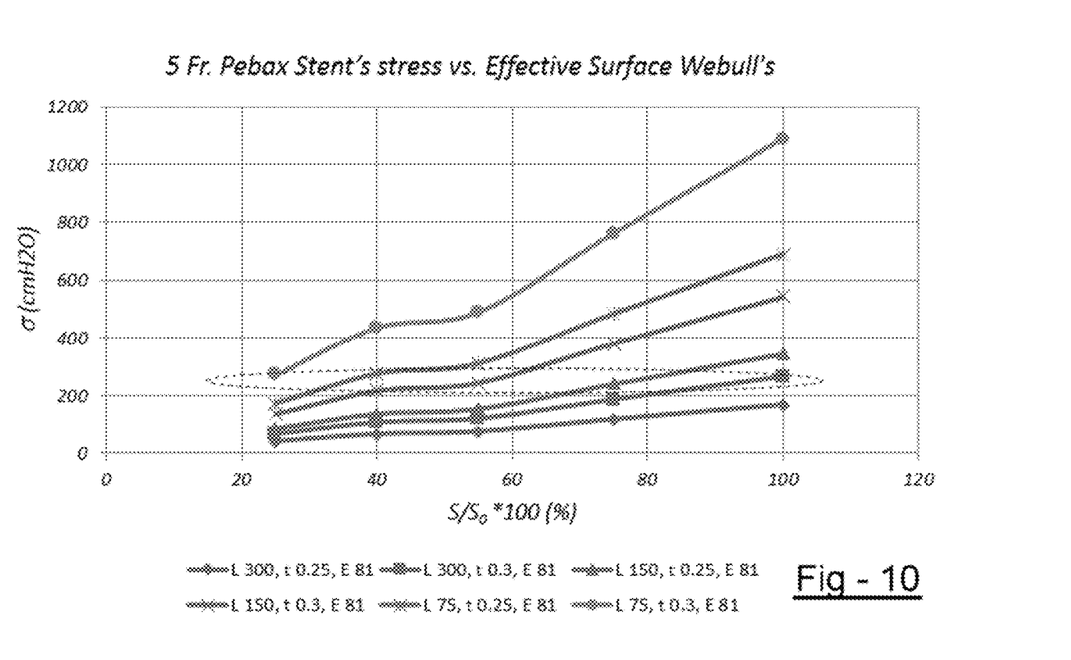
FIG. 10 is a graph illustrating Stress ($\sigma$) on the stent vs. % of Surface area of stent ($S_0$)/Surface area of stent having cuts (S) (i.e., $S_0/S$); the stent having a 5 Fr. size and made of Pebax® material.

Referring specifically to FIG. 10, dix different stents having a 5 Fr. size made of Pebax® material having a modulus of elasticity of 81 MPA were tested.

As illustrated in FIG. 10, a first stent with a length of 300 mm and thickness of 0.25 mm did not fall within the pressure range of 200 cm H2O to 225 cm H2O at about 82 S/$S_0$ to about 100 S/$S_0$. A second stent with a length of 300 mm and thickness of 0.30 mm fell within the pressure range of 200 cm H2O to 225 cm H2O at about 75 S/$S_0$ to about 98 S/$S_0$. A third stent with a length of 150 mm and thickness of 0.25 mm fell within the pressure range of 200 cm H20 to 225 cm H2O at about 65 S/$S_0$ to about 83 S/$S_0$. A fourth stent with a length of 150 mm and thickness of 0.30 mm fell within the pressure range of 200 cm H2O to 225 cm H2O at about 38 S/$S_0$ to about 61 S/$S_0$. A fifth stent with a length of 75 mm and thickness of 0.25 mm fell within the pressure range of 200 cm H2O to 225 cm H2O at about 30 S/$S_0$ to about 40 S/$S_0$. A sixth stent with a length of 75 mm and thickness of 0.30 mm fell within the pressure range of 200 cm H2O to 225 cm H2O at about 25 S/$S_0$.

Figure 11:
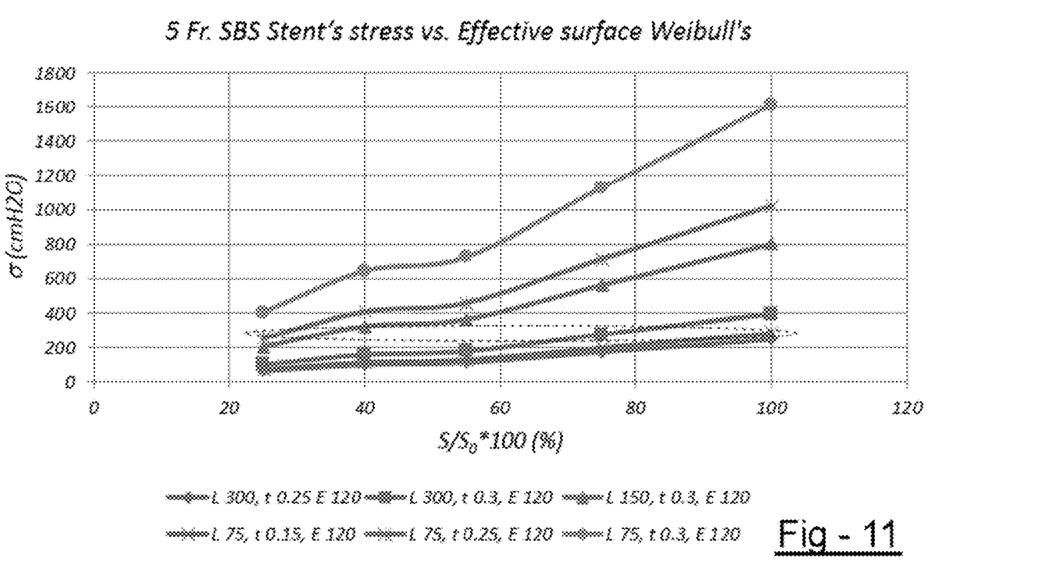
FIG. 11 is a graph illustrating Stress ($\sigma$) on the stent vs. % of Surface area of stent ($S_0$)/Surface area of stent having cuts (S) (i.e., $S_0/S$); the stent having a 5 Fr. size and made of SBS material.

Referring specifically to FIG. 11, six different stents having a 5 Fr. size made of SBS material having a modulus of elasticity of 120 MPA were tested.

As illustrated in FIG. 11, a first stent with a length of 300 mm and thickness of 0.25 mm fell within the pressure range of 200 cm H2O to 225 cm H2O at about 100 S/$S_0$. A second stent with a length of 300 mm and thickness of 0.30 mm fell within the pressure range of 200 cm H2O to 225 cm H2O at about 65 S/$S_0$ to about 90 S/$S_0$. A third stent with a length of 150 mm and thickness of 0.30 mm fell within the pressure range of 200 cm H2O to 225 cm H2O at about 30 S/$S_0$ to about 55 S/$S_0$. A fourth stent with a length of 75 mm and thickness of 0.15 mm fell within the pressure range of 200 cm H2O to 225 cm H2O at about 100 S/$S_0$. A fifth stent with a length of 75 mm and thickness of 0.25 mm fell within the pressure range of 200 cm H2O to 225 cm H2O at about 25 S/$S_0$ to about 30 S/$S_0$. A sixth stent with a length of 75 mm and thickness of 0.30 mm did not fall within the pressure range of 200 cm H2O to 225 cm H2O.

Figure 12:
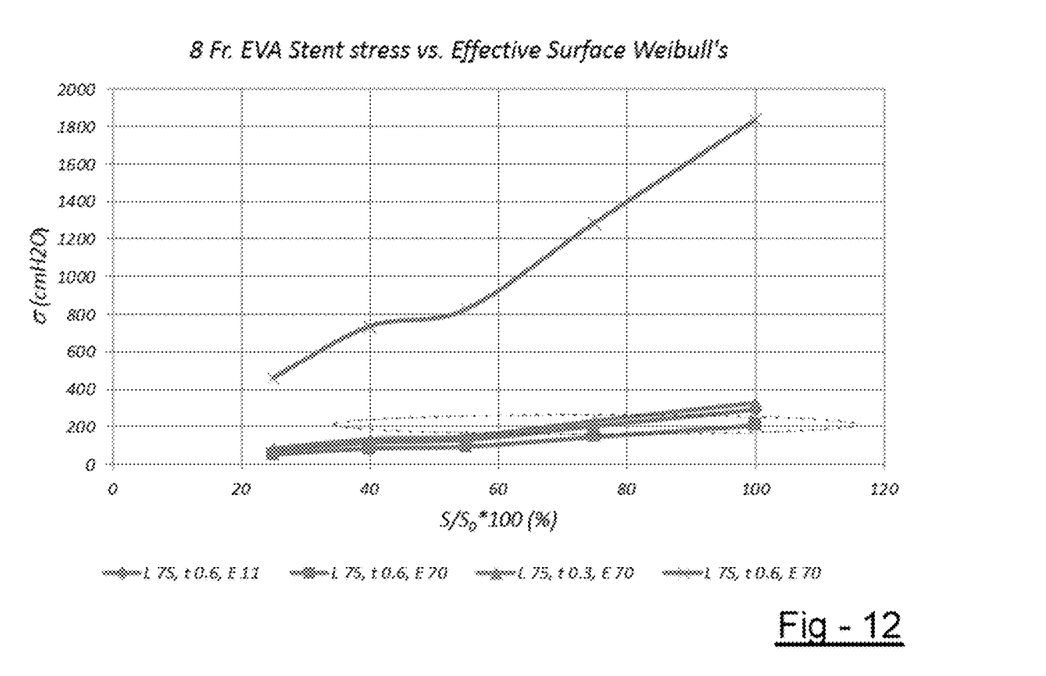
FIG. 12 is a graph illustrating Stress ($\sigma$) on the stent vs. % of Surface area of stent ($S_0$)/Surface area of stent having cuts (S) (i.e., $S_0/S$); the stent having a 8 Fr. size and made of EVA material.

Referring specifically to FIG. 12, four different stents having a 8 Fr. size made of EVA material were tested.

As illustrated in FIG. 12, a first stent with a length of 75 mm and thickness of 0.60 mm fell within the pressure range of 200 cm H2O to 225 cm H2O at about 62 S/$S_0$ to about 92 S/$S_0$. A second stent with a length of 75 mm and thickness of 0.60 mm fell within the pressure range of 200 cm H2O to 225 cm H2O at about 75 S/$S_0$ to about 100 S/$S_0$. A third stent with a length of 75 mm and thickness of 0.30 mm fell within the pressure range of 200 cm H2O to 225 cm H2O at about 60 S/$S_0$ to about 85 S/$S_0$. A fourth stent with a length of 75 mm and thickness of 0.60 mm did not fall within the pressure range of 200 cm H2O to 225 cm H2O.

Figure 13:
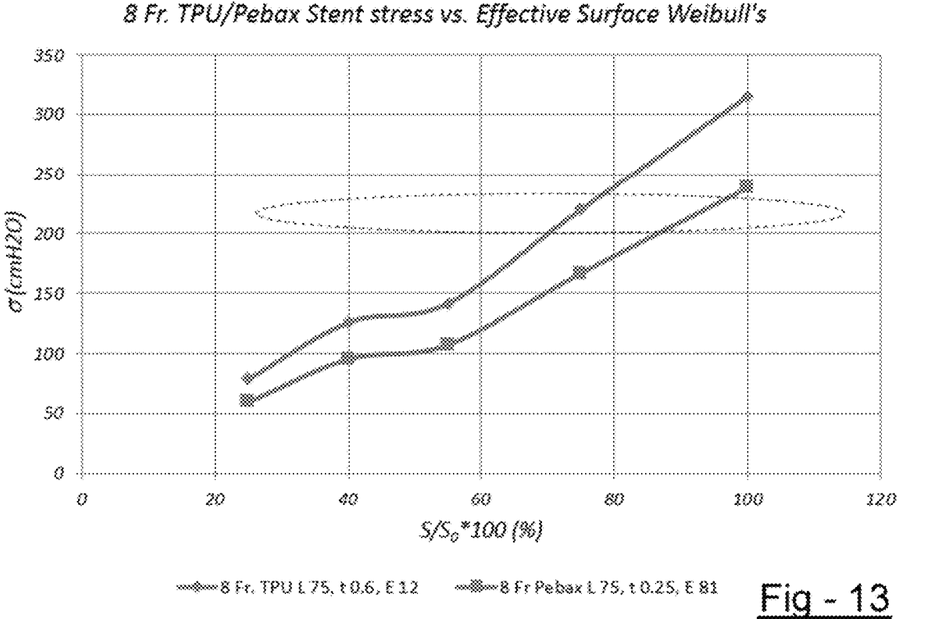
FIG. 13 is a graph illustrating Stress ($\sigma$) on the stent vs. % of Surface area of stent ($S_0$)/Surface area of stent having cuts (S) (i.e., $S_0/S$); the stent having a 8 Fr. size and made of a TPU/Pebax® material.

Referring specifically to FIG. 13, two different stents having a 8 Fr. size made of a TPU and Pebax® material were tested.

As illustrated in FIG. 13, a first stent with a length of 75 mm, thickness of 0.60 mm, TPU material having modulus of elasticity of 12 fell within the pressure range of 200 cm H2O to 225 cm H2O at about 70 S/$S_0$ to about 79 S/$S_0$. A second stent with a length of 75 mm, a thickness of 0.25 mm, a Pebax® material having modulus of elasticity of 81 fell within the pressure range of 200 cm H2O to 225 cm H2O at about 85 S/$S_0$ to about 98 S/$S_0$.

Figure 14:
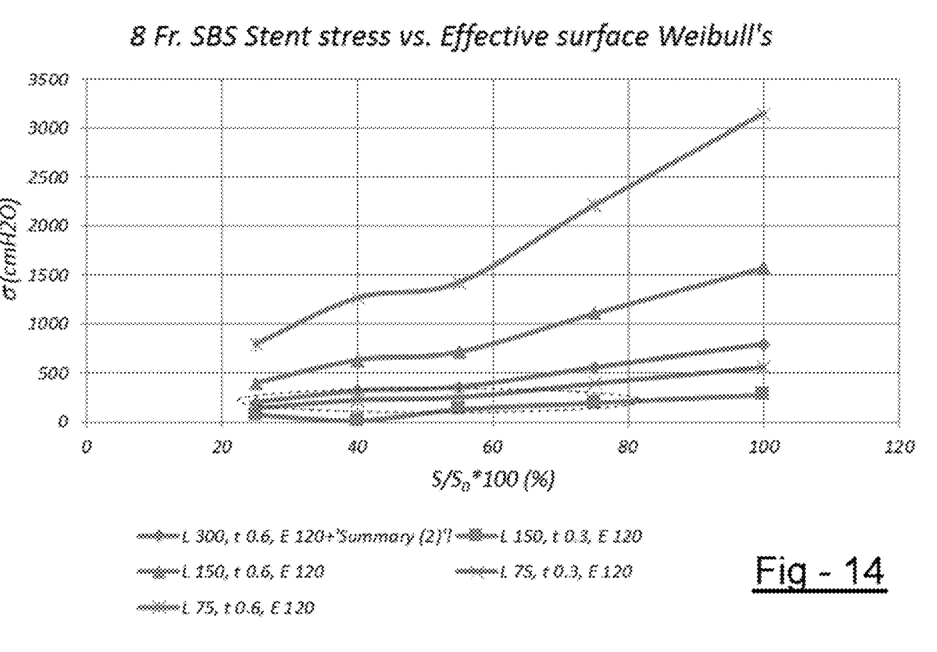
FIG. 14 is a graph illustrating Stress ($\sigma$) on the stent vs. % of Surface area of stent ($S_0$)/Surface area of stent having cuts (S) (i.e., $S_0/S$); the stent having a 8 Fr. size and made of a SBS material.

Referring specifically to FIG. 14, five different stents having a 8 Fr. size made of a SBS material having modulus of elasticity of 120 were tested.

As illustrated in FIG. 14, a first stent with a length of 300 mm, thickness of 0.60 mm, did not fall within the pressure range of 200 cm H2O to 225 cm H2O. A second stent with a length of 150 mm and a thickness of 0.30 mm fell within the pressure range of 200 cm H2O to 225 cm H2O at about 55 S/$S_0$ to about 75 S/$S_0$. A third stent with a length of 150 mm and a thickness of 0.60 mm did not fall within the pressure range of 200 cm H2O to 225 cm H2O. A fourth stent with a length of 75 mm and a thickness of 0.30 mm fell within the pressure range of 200 cm H2O to 225 cm H2O at about 25 S/$S_0$ to about 70 S/$S_0$. A fifth stent with a length of 75 mm, thickness of 0.60 mm, did not fall within the pressure range of 200 cm H2O to 225 cm H2O.

REFERENCE NUMERALS 10 urinary tract
12 kidney
14 bladder
100 ureteral stent
102 tubular member
104 first retaining end
106 second retaining end
108 cuts
110 linear portion
112 first loop
114 position of retaining end
116 second loop
118 position of retaining end
120 third loop
122 position of retaining end
124 fourth loop 126 position of retaining end 104, 106; terminal end of retaining end 104, 106'
128 loop axis
130 loop axis
132 loop axis
134 section of retaining end 104, 106
134' bulge
136 section of retaining end 104, 106
136' bulge
138 section of retaining end 104, 106
138' bulge
140 portion of retaining end 104, 106
142 portion of retaining end 104, 106

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

By use of the term "may" herein, it is intended that any described attributes that "may" be included are optional.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A ureteral stent comprising:
   a tubular member comprising an interior surface; and
   a retaining end at an end of the tubular member, where the retaining end is adapted to be placed inside a kidney or a bladder of a patient, where the retaining end comprises a plurality of openings around the tubular member, and where the retaining end is configured to deform outward when a force is exerted on the interior surface of the tubular member at the retaining end by fluid pushing outward against the interior surface proximate the plurality of openings.

2. The ureteral stent according to claim 1, wherein the retaining end comprises a plurality of sections, where each of the plurality of sections comprises one or more of the openings.

3. The ureteral stent according to claim 2, wherein after the force is exerted on the interior surface of the tubular member, the retaining end is configured to be moved into a deployed configuration and, in the deployed configuration, the retaining end is configured to deform at one or more of the plurality of sections, and
   wherein a bulge is formed at each of the plurality of sections.

4. The ureteral stent according to claim 3, wherein the bulge has a spherical shape.

5. The ureteral stent according to claim 3, wherein a diameter of the bulge closest to a terminal end of the retaining end is larger than a diameter of the bulge furthest from the terminal end.

6. The ureteral stent according to claim 5, wherein a length of the openings in the bulge closest to the terminal end are longer than a length of the openings in the bulge furthest from the terminal end.

7. The ureteral stent according to claim 3, wherein in between two adjacent bulges, the retaining end comprises a portion that is free of any openings.

8. The ureteral stent according to claim 7, wherein the portion that is free of any openings has a diameter that is equivalent to a diameter of the tubular member.

9. The ureteral stent according to claim 1, wherein the force comprises fluid pressure of urine that is passed through the ureteral stent.

10. A method comprising:
    inserting the ureteral stent according to claim 1 into an anatomy of a patient, and
    subjecting the tubular member to the force exerted on the interior surface of the tubular member at the retaining end by the fluid pushing outward against the interior surface proximate the plurality of openings to deform the retaining end.

11. The method according to claim 10, wherein the retaining end comprises one or more sections having the plurality of openings, and a bulge is formed at each of the one or more sections after the tubular member is subjected to the force.

12. The method according to claim 11, wherein a diameter of the bulge closest to a terminal end of the retaining end is larger than a diameter of the bulge furthest from the terminal end.

13. A ureteral stent comprising:

a tubular member comprising an interior surface; and a retaining end adapted to be placed inside a kidney or a bladder of a patient and configured to deform when a fluid pressure is exerted on the interior surface of the tubular member, wherein the retaining end is configured such that, after the fluid pressure is exerted on the interior surface of the tubular member, the retaining end is moved into a deployed configuration and in the deployed configuration, the retaining end is configured to deform at one or more of the one or more sections, wherein a bulge is formed at each of the one or more sections, wherein a third bulge is formed between the bulge closest to the terminal end of the retaining end and the bulge furthest from the terminal end, wherein a diameter of the third bulge is smaller than the diameter of the bulge closest to the terminal end, the diameter of the third bulge is larger than the diameter of the bulge furthest from the terminal end.

14. The ureteral stent according to claim 1, wherein the retaining end is configured to be moved into a deployed configuration after the force is exerted on the interior surface of the tubular member, and the retaining end consists of only three bulges when the retaining end is in the deployed configuration.

15. The ureteral stent according to claim 14, wherein the retaining end is configured to be moved into an undeployed configuration when there is little or no fluid pressure exerted on the interior surface of the tubular member, and in the undeployed configuration, the three bulges contract.

16. The ureteral stent according to claim 1, wherein the retaining end is configured to be moved into a deployed configuration after the force is exerted on the interior surface of the tubular member, and the retaining end consists of only one bulge when the retaining end is in the deployed configuration.

17. The ureteral stent according to claim 16, wherein the retaining end is configured to be moved into an undeployed configuration when there is little or no fluid pressure exerted on the interior surface of the tubular member, wherein the undeployed configuration, the one bulge contracts.

18. The ureteral stent according to claim 3, wherein the retaining end is configured to be moved into an undeployed configuration when there is little or no fluid pressure exerted on the interior surface of the tubular member, in the undeployed configuration, wherein the bulge that is formed at each of the one or more sections having the plurality of openings contracts.

19. The ureteral stent according to claim 1, wherein a material of the retaining end is a swelling polymer that is configured to deform when in contact with a fluid.

20. The ureteral stent according to claim 14, wherein a material of the retaining end is a swelling polymer that is configured to deform when in contact with a fluid.

* * * * *

UNITED STATES PATENT AND TRADEMARK OFFICE
CERTIFICATE OF CORRECTION

| | | |
|---|---|---|
| PATENT NO. | : 10,933,227 B2 | Page 1 of 1 |
| APPLICATION NO. | : 15/829092 | |
| DATED | : March 2, 2021 | |
| INVENTOR(S) | : Walish et al. | |

It is certified that error appears in the above-identified patent and that said Letters Patent is hereby corrected as shown below:

On the Title Page

Item (72), in "Inventors", in Column 1, Line 2, delete "Action," and insert --Acton,-- therefor Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*